(12) United States Patent
Katopodis

(10) Patent No.: US 7,262,058 B2
(45) Date of Patent: Aug. 28, 2007

(54) METHOD FOR DETERMINING LIPID ASSOCIATED SIALOPROTEIN IN BODY FLUIDS

(76) Inventor: Nonda Katopodis, 5200 N. Ocean Dr., Singer Island, FL (US) 33404

( * ) Notice: Subject to any disclaimer, the term of this patent is extended or adjusted under 35 U.S.C. 154(b) by 692 days.

(21) Appl. No.: 09/802,457

(22) Filed: Mar. 9, 2001

(65) Prior Publication Data
US 2002/0127729 A1    Sep. 12, 2002

(51) Int. Cl.
*G01N 33/48* (2006.01)
*G01N 33/487* (2006.01)
*C07K 1/02* (2006.01)
*C01K 1/14* (2006.01)
*C01K 1/30* (2006.01)

(52) U.S. Cl. .................. 436/64; 436/71; 436/813; 436/815; 530/419; 530/420; 530/424; 530/428

(58) Field of Classification Search .................. 436/64, 436/813; 530/395, 412, 418, 419, 422, 426, 530/828, 836, 407, 420, 424, 427; 435/4
See application file for complete search history.

(56) References Cited

U.S. PATENT DOCUMENTS

| | | | |
|---|---|---|---|
| 5,045,453 A | * | 9/1991 | Katopodis |
| 5,236,927 A | * | 8/1993 | Jones et al. ............ 514/19 |
| 5,296,346 A | * | 3/1994 | Katopodis ............ 435/4 |

FOREIGN PATENT DOCUMENTS

WO    WO 92/08976    *    5/1992

OTHER PUBLICATIONS

Gernez-Rieux et al, Pathologie Biologie, 1963, vol. 11, pp. 729-741.*
Figarella-Branger et al, Cancer Reearch, 1990, vol. 50, pp. 6334-6370.*
Rao, Trans All-India Institute of Mental Health, 1999, vol. 9, pp. 35-38.*
Bellahcene et al, British Journal of Haematology, 2000, vol. 111, pp. 1118-1121.*
Burger et al, Neurol Clin, vol. 9, pp. 249-271. (abstract).*
Ross et al, Surg Neurol, 1991, vol. 36, pp. 431-440. (abstract).*
Chondros et al (Anticancer Research, 1991, vol. 11, pp. 2103-2106)*
Stoscheck (Quantitation of Protein, In: Guide to Protein Purification, Deutscher, Ed., 1990, pp. 50-68).*

* cited by examiner

*Primary Examiner*—Karen A. Canella
(74) *Attorney, Agent, or Firm*—Paul L. Bollo, Esq.

(57) ABSTRACT

The amount of lipid associated sialoprotein (LSP) in body fluids such as cerebrospinal fluid, peritoneal fluid, pleural fluid, bronchial washings, saliva and sputum samples, may be determined by a method which may be automated, involving the following steps to be performed on the sample: adding a mixture of a chlorinated lower alkyl alcohol; centrifuging to yield a substantially clear upper phase; recovering the upper phase and adding to it a protein precipitating agent; mixing the resulting admixture; recovering the resulting precipitate; washing the precipitate with saline solution; centrifuging to recover the precipitate; dissolving the precipitate in water; mixing; adding to the resulting mixture an hydrolysis agent; heating; and determining the amount of lipid associated sialoprotein present by determining the optical density of the sample.

18 Claims, 6 Drawing Sheets

MPBT : Malignant primary brain tumors
BPBT: Benign primary brain tumors
MBT: Metastatic brain tumors
ST: Systemic tumors without brain metastasis.
NNC: Nonrmal neurologic controls
NC: Neurologic controls LONGITUDINAL STUDIES OF PATIENTS
UNDER TREATMENT
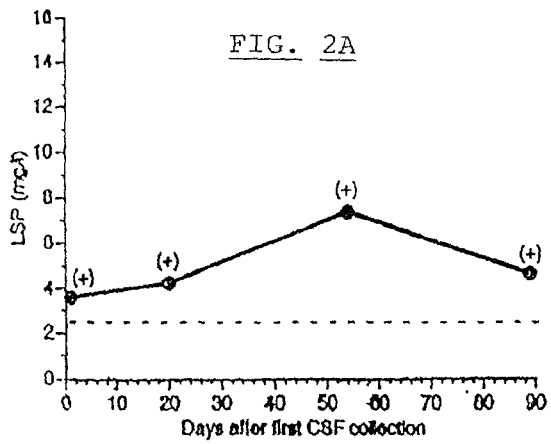
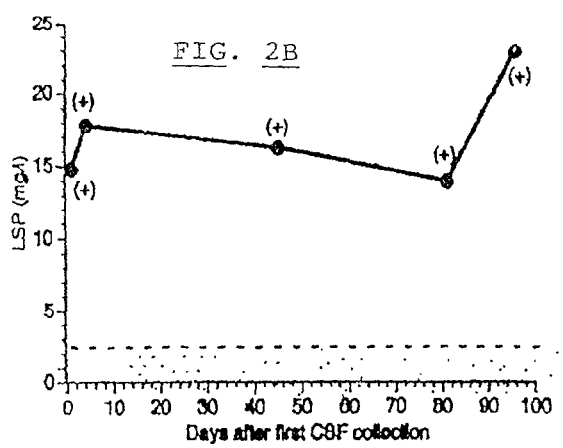
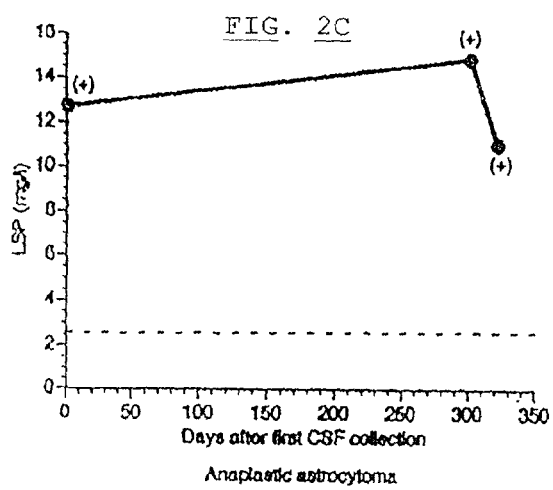
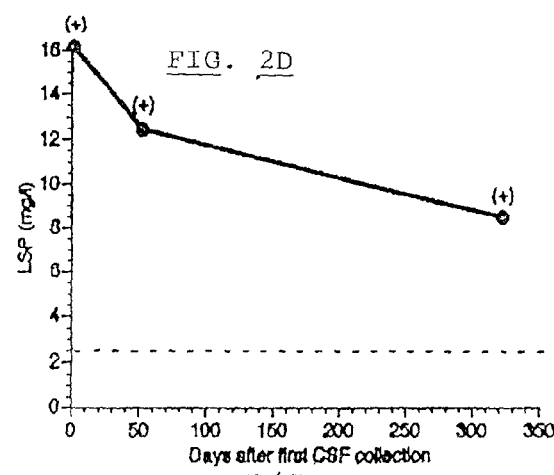

MPBT: Malignant primary brain tumors
BPBT: Benign primary brain tumors

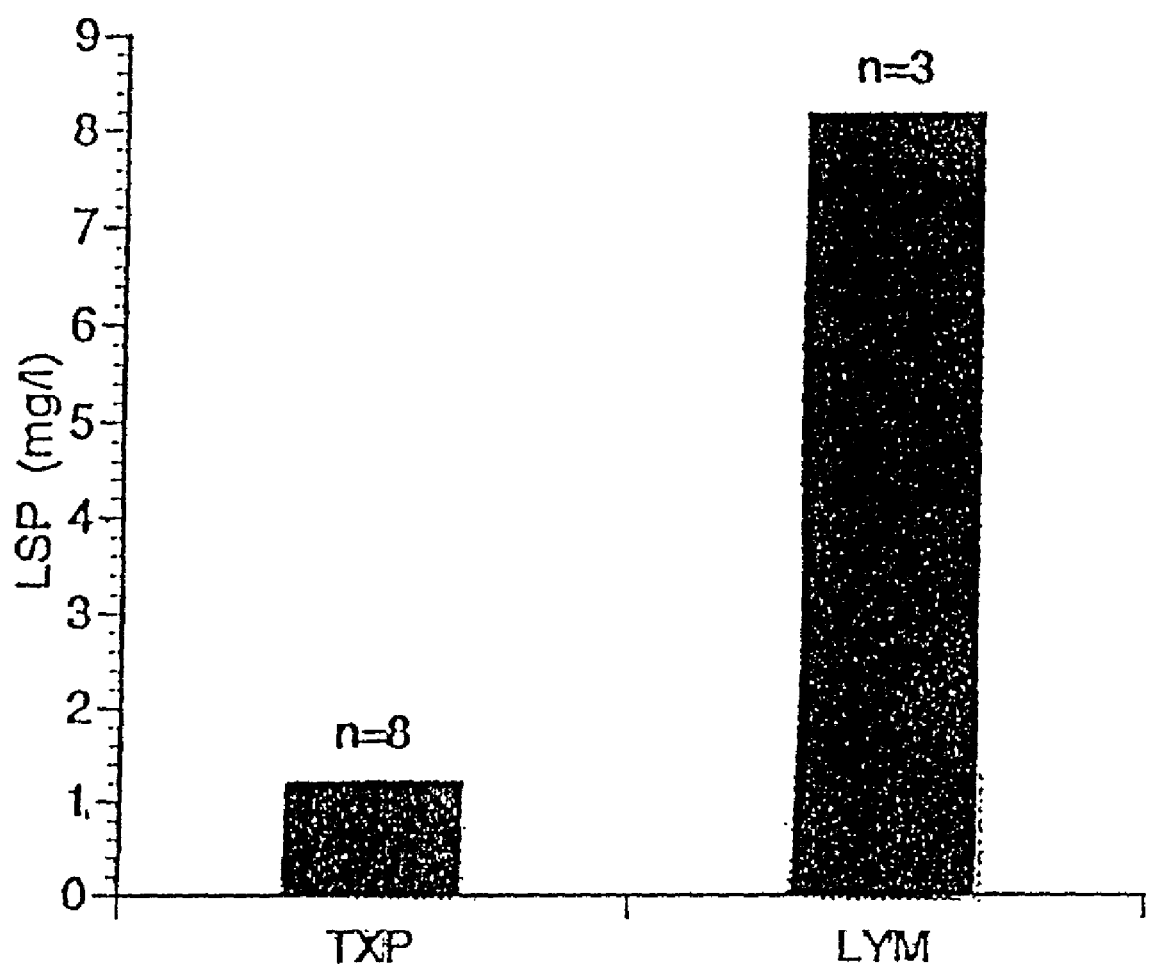

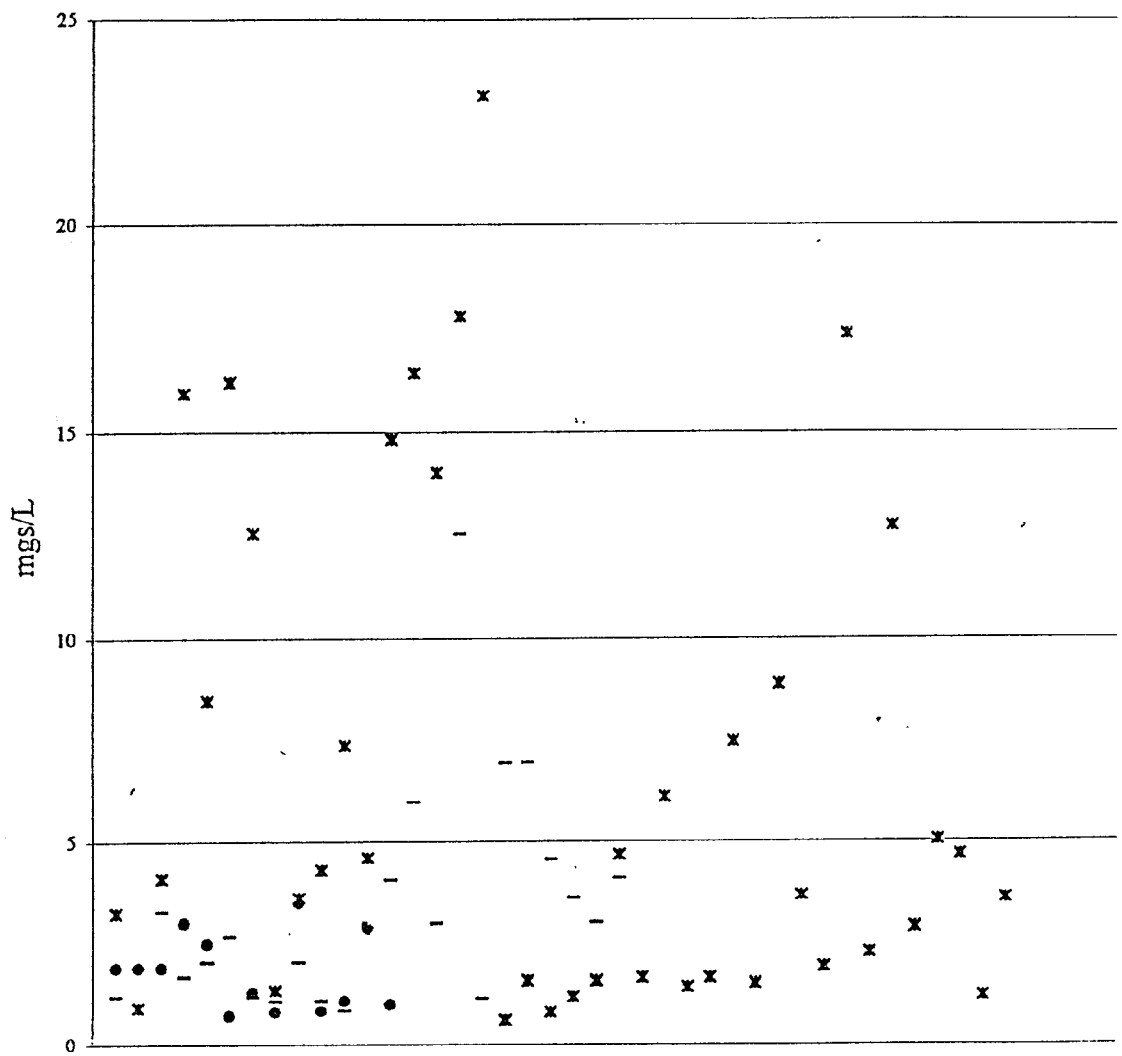

METHOD FOR DETERMINING LIPID ASSOCIATED SIALOPROTEIN IN BODY FLUIDS

BACKGROUND OF THE INVENTION

This invention pertains to a method of identifying patients with brain tumors and to determine the response of patients to treatment. The method of the invention can distinguish patients with malignant primary and metastatic brain tumors by measuring the increase of lipid associated sialoprotein (LSP) in the cerebrospinal fluid (CSF). The invention also can determine the response to treatment and therefore it can be used to monitor radiation and chemotherapy.

There exist other methods and procedures for distinguishing patients with malignant brain tumors from benign tumors. However, these methods typically require tumor tissue which is not practical on a routine basis or sophisticated equipment such as MRI spectroscopy which is expensive and not widely available. On the other hand, CSF is easily and safely accessible in nearly all patients and can be examined at reasonably frequent intervals without comprising a patient's safety. Moreover, MRI scanning is frequently unrevealing or equivocal with respect to early indications of central nervous system attack by systemic tumor metastasis.

The method of the invention whereby LSP is measured in the CSF has been shown to provide an early indicator of central nervous system involvement. Prior to the method of the invention there has been no specific tumor marker for brain cancer. Moreover, the method of the invention is extremely cost effective, particularly when compared with the significant cost associated with an MRI examination.

More than one hundred thousand new cases of brain tumors were diagnosed in 1998. By the time the symptoms appear most tumors have infiltrated widely and surgery, cranial irradiations and chemotherapy can provide only questionable benefit. Diagnosis of brain tumors generally occur after the onset of neurologic manifestations. By that time the tumor is well established and for the vast majority of patients this is fatal. Modern neuroimaging techniques such as magnetic resonance imaging (MRI), spectroscopy, and position emission tomography have facilitated early diagnosis. However, these studies are expensive and cumbersome and are limited by false negative and false positive findings in a number of common situations including radiation necrosis, central nervous system infections, or vascular malformations. A convenient, reliable and efficient screening test which can detect brain metastases at an early stage to initiate treatment in patients at high risk has not been currently available. Also lacking is a reliable method to detect tumor reoccurrence, predict response to therapy, and distinguish between persistent or recurrent tumor and treatment related changes in patients with primary brain tumors.

A number of antigens have been suggested as tumor serologic markers. For example, there are squamous cell carcinoma antigen, prostate specific antigen, carcinoma embryonic antigen, and antigens labeled CA 125 for ovarian cancer, CA 153 for breast cancer and CA 19-9 for pancreatic cancer. These markers are serologic markers identified in the blood for systemic tumors but no such markers have been found in the blood of patients with primary brain tumors. Most brain tumor markers reflect chromosomal abnormalities such as gene mutations, translocations, and fibroblasts growth factor expression. However, these markers are determined only when biopsy specimens are obtained and the tumors themselves are analyzed. They are not useful as diagnostic aids or to assess a response to ongoing therapy.

The method of the invention makes use of cerebro spinal fluid (CSF) as a source of biological indicators that can provide information regarding the presence of a tumor in the CSF and its status. The method of the invention shows that CSF contains specific markers which provide a basis for evaluating the presence of a tumor in the CSF or its activity.

It has long been known that tumor cells have caused changes in the metabolism of sialic acid. These changes result in larger amounts of sialic acid being present on the surface of malignant tumor cells compared to benign tumor cells.

It was suggested that Sialic Acid (S.A.) might be a useful tumor marker 25 years ago when a new protein lipid complex was identified in rats with Walker adenocarcinoma. In 1977 Kloppel and his collaborators for the first time used serum S.A. as a marker for cancer. The most commonly used method is one developed by Katopodis e. al. LSA has been found to be more reliable than other markers in identifying patients with head and neck cancer, localized and metastatic prostate cancer, lung cancer, leukemia, lymphoma, Hodgkins' lymphoma, melanoma and others.

These serologic markers of the prior art are principally identified in the blood for systemic tumors. The method of the invention makes use of the CSF and has determined that material produced by the tumor or the surrounding cells in response to the tumor are diffused into the CSF.

SUMMARY OF THE INVENTION

The present invention provides a method to determine the levels of lipid associated sialoprotein (LSP) in the cerebrospinal fluid (CSF) which includes the following steps:
a) obtaining a CSF sample in the amount of 500 ul. No dilution is necessary because the sample by its nature is very diluted. This fact also dictates that a larger sample is required.
b) adding to the sample mixture of a chlorinated lower alkyl hydrocarbon and a lower alkyl alcohol, the volume and ratio of chlorinated hydrocarbon to alcohol in the mixture being approximately 2 to 1;
c. centrifuging to obtain a clear upper phase;
d. extracting the upper phase resulting from said mixing;
e. treating predetermined amounts of said upper phase with a protein precipitating agent having a predetermined concentration;
f. centrifuging the admixture for a suitable period of time and washing the precipitate with saline solution in a predetermined amount;
g. centrifuging the resulting admixture for a suitable period of time;
h. dissolving the precipitate in a buffer solution;
i. treating the mixture with a hydrolysis agent;
j. heating the resulting mixture at a predetermined temperature for a predetermined time; and
k. determining the amount of lipid associated sialoprotein in the suspended precipitate and thereby the amount present in the CSF sample.

The determination of the amount of lipid associated sialoprotein in the sample is made by comparing the optical density of the sample to that of a known concentration of standard.

The method of the invention provides a reliable test to distinguish between malignant brain tumors and benign brain tumors. The invention also provides a method for monitoring a patient's response to treatment.

BRIEF DESCRIPTION OF THE FIGURES

FIG. 2 shows the correlation of LSP in longitudinal studies of patients with brain tumors under radiation and chemotherapy.

FIG. 5 shows the higher concentration of LSP in the CSF of patients with lymphoma and a much lower concentration in patients with HIV and toxoplasmosis.

FIG. 6 charts the concentration of LSP in the CSF of control samples (dizziness, headaches, strokes and the like), of neurological samples (lyme disease, Alzheimer's, Meningitis) and of samples from patients having malignancies in different stages.

DETAILED DESCRIPTION OF THE INVENTION

Figure 1:
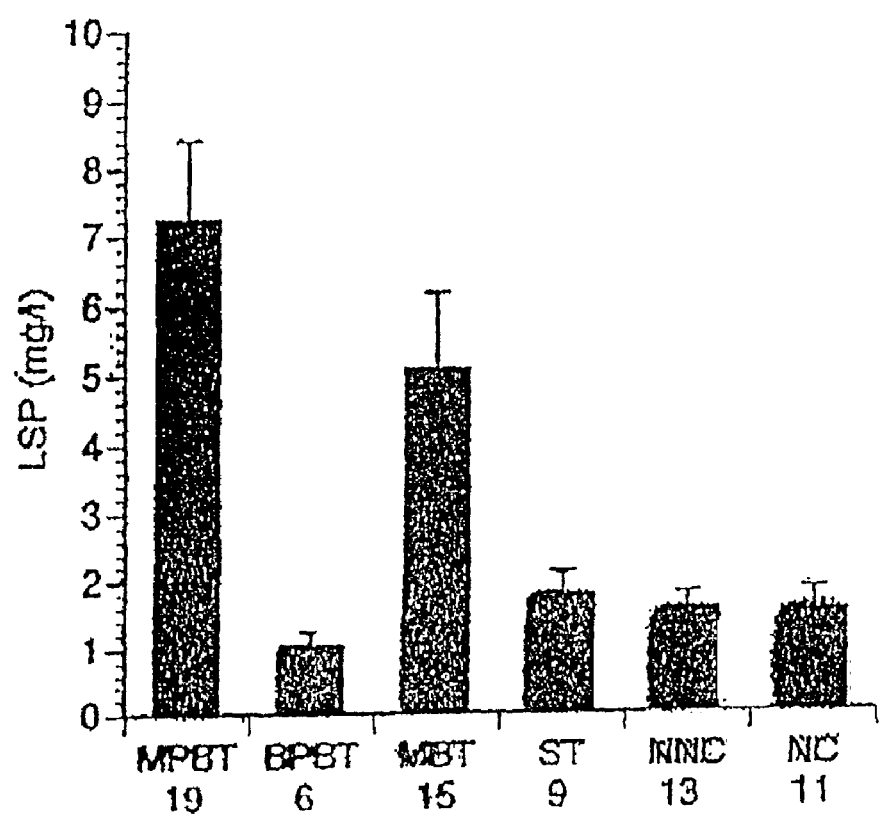
FIG. 1 shows the concentration of LSP in the CSF patients with and without brain tumors. It can be seen that the concentration of LSP is significantly higher in patients with malignant primary brain tumors and metastatic brain tumors as compared to those with benign primary brain tumors, systemic malignant tumors without brain metastasis, and neurologic controls (dizziness, headaches, strokes, lyme disease, alzheimers and HIV).

The amount of LSP in a sample of CSF may be determined and the amount determined used as a diagnostic indicator of brain tumors. A preliminary step to the method is to obtain a sample to be tested. A sample will typically be recovered by means of lumbar puncture whereby CSF is easily and safely accessible in nearly all patients and can be examined at reasonably frequent intervals without compromising the patient's safety.

The initial amount of the CSF sample must be in the amount of 500 ul. The present invention eliminates the need for diluting as in the prior art because the LSP is highly diluted in CSF. It is this high dilution that requires a larger sample of CSF than of the samples of the prior art.

The sample is then treated with a mixture of a chlorinated lower alkyl hydrocarbon and a alkyl alcohol in which the volume ratio of chlorinated hydrocarbon to alcohol is about 2 to 1. The volume of the hydrocarbon alcohol mixture added to the sample is approximately 750 ul which is a much smaller volume than the prior art because of the elimination of the dilution step in the prior art. Water or buffer for partitioning is not added as in the prior art since contaminants will dissolve from the interface to the upper phase. Contaminants are other soluble proteins and glycoproteins, also pigments from hemoglobin from hemolysed blood (resulting from injury during CSF collection) which will increase the final color in reaction with the resorcinol agent. Suitable chlorinated hydrocarbons include chloroform, methylene chloride and ethylene chloride, chloroform being presently preferred. The lower alkyl may be methanol, ethanol, propanol, n-butanol or the like.

The resulting admixture is then centrifuged at 3500 rpm for 5 minutes to obtain a substantially clear upper phase.

The predetermined volume of the upper phase is then separately recovered from the substantially clear upper phase so formed in a volume that was predetermined by the volume of the original CSF sample. If the original volume of the predetermined CSF sample is 500 ul, the volume of the upper phase separately recovered will be 500 ul.

This predetermined volume of the upper phase is then treated with the protein precipitating agent such as aqueous phosphotungstic acid solution in a concentration in the range of 0.3 to 0.6 milligrams per milliliter. The amount of the protein precipitating agent (PTA) in the solution is far more diluted than the one used in the prior art. This low concentration of PTA is selectively precipitating the LSP because this concentration of PTA affects the isoelectric point of the protein existing in the LSP complex. Higher concentrations of PTA as in the prior art would coprecipitate still existing contaminants in the upper phase such as other proteins and glycoproteins present in CSF thus producing a contaminated precipitate and adversely affecting the results of the method of the invention. On the other hand a concentration lower than 0.03 mg/ml would not be enough to precipitate quantitatively the LSP.

The resulting admixture is centrifuged between 6000 and 6100 rpm for 5 minutes to produce a resulting precipitate. A lower rpm does not complete the precipitation while a higher rpm makes the precipitate solid so that only part of the precipitate is exposed to washing with saline solution and thus not all of the contaminants are removed. The supernatant is decanted and the remaining precipitate is washed with 500 ul of saline solution to remove any traces of contaminants. It is essential that saline solution and not water be used to wash the precipitate as the saline solution is effective in removing the contaminants which have been precipitated as a result of the isoelectric precipitation of the protein of the LSP as described above. The resulting admixture is then centrifuged at 3500 rpm for 5 minutes to form a clear precipitate. The supernatant again is decanted. The resulting precipitate is then dissolved in 200 microliters of distilled water.

The resulting admixture is then hydrolized with resorcinol reagent in a heating block at a temperature between 115 to 120 degrees centigrade over a period of 15 minutes. It is important that the temperature be increased to 120 degrees during this heating step in order to complete the hydrolysis of the LSP complex and to completely destroy the remaining contaminants after purification and washing. Maintaining the temperature in this narrow range is essential to the method of the invention because at a lower temperature the hydrolysis will be incomplete (less color and less accuracy) while at a higher temperature the hydrolized components of the complex will turn to a dark brown color interfering with the blue color measured at 580 nm as described below.

The mixture is then treated with a mixture of butyl acetate and n-butanol in a ratio of 85 to 15 by volume and then treated by mixing, centrifuging, separating the organic layer, reading at 580 mm the extracted blue color present in the organic layer and determining the amount of LSP in the sample by comparing the optical density of the sample with the standard curve developed by a standard sample of n-acetyl neuraminic acid.

Figure 3:
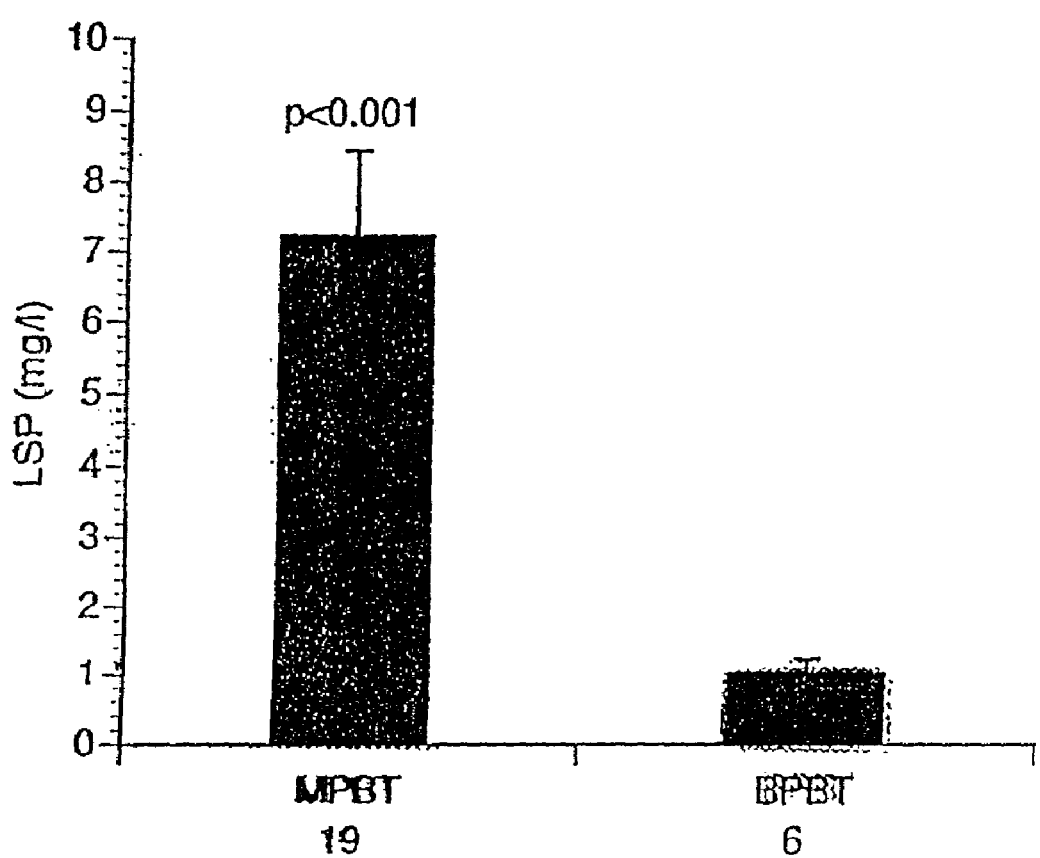
FIG. 3 shows the significantly increased concentration of LSP in the CSF of patients with malignant primary brain tumors and a much lower concentration in patients with benign primary brain tumors.
Figure 4:
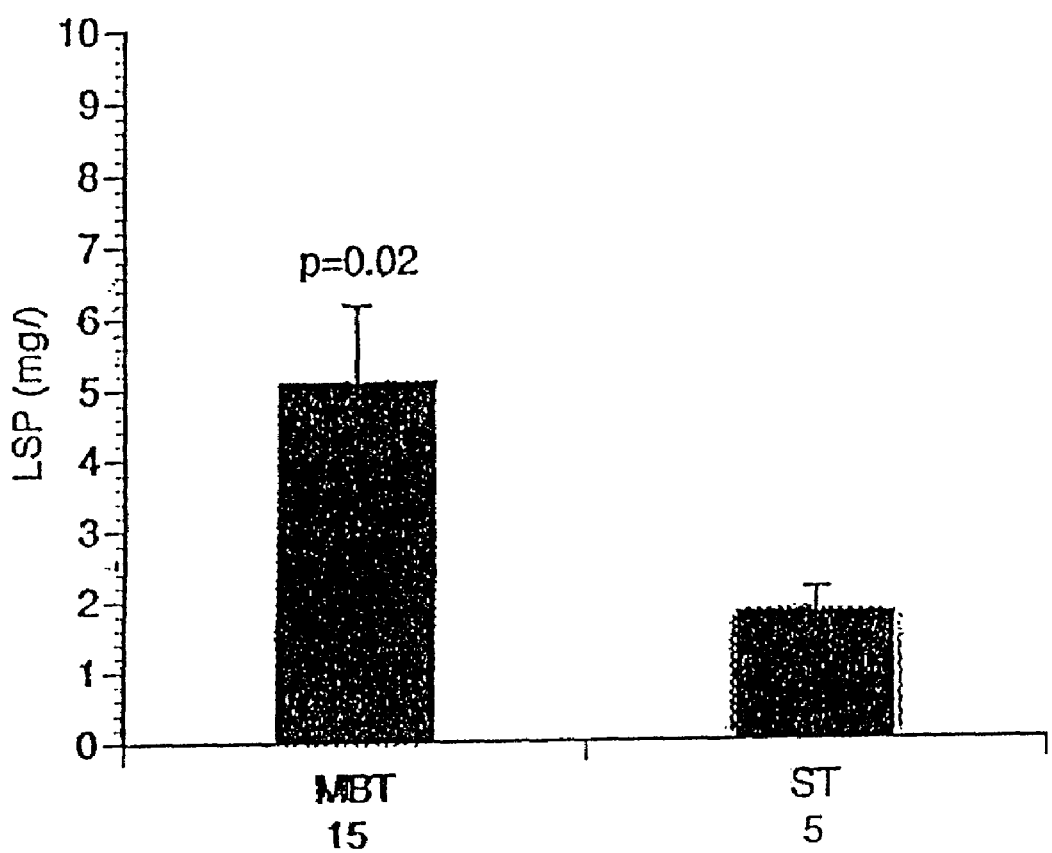
FIG. 4 compares the increased concentration of LSP in the CSF of patients with metastatic brain tumors versus patients who do not have metastatic brain tumors.

The reliability and accuracy of the present invention can be seen from the enclosed FIGS. 1-6.

What is claimed is the following:

1. A method of extracting lipid associated sialoprotein from cerebrospinal fluid of human subjects having or suspected of having cancer, and determining the amount of lipid associated sialoprotein in a sample of such fluid which comprises the following steps:
   a) adding to the sample a mixture of a chlorinated lower alkyl hydrocarbon and a lower alkyl alcohol;

b) mixing the resulting admixture for a suitable period of time to dissolve lipid-bound sialic acid in the sample in the chlorinated hydrocarbon/alcohol mixture;

c) centrifuging the mixture at about 6000 rpm to form a substantially clear upper phase;

d) separately recovering from the clear upper phase so formed a predetermined volume of the upper phase;

e) adding to the predetermined volume of the upper phase an amount of a mixture of an aqueous protein-precipitating agent without any adsorbing material, the amount of mixture being effective to cause precipitation of the lipid associated sialoprotein;

f) vortexing the resulting admixture;

g) centrifuging and recovering the resulting precipitate;

h) washing the precipitate in a saline solution;

i) centrifuging the resulting mixture;

j) dissolving the precipitate in water;

k) adding to the solution a hydrolysis agent;

l) heating the resulting admixture;

m) determining the amount of lipid associated sialoprotein present in the solution and thereby the amount present in the fluid sample.

2. A method according to claim 1, wherein in step(a) the volume of the added mixture is about 750 ul.

3. A method according to claim 1, wherein in step(a) the lower alkyl alcohol is metanol, ethanol, porpanol, n-butanol, isopropanol, isobutanol or isoamyl alcohol.

4. A method according to claim 1, wherein in step(a) the chlorinated lower alkyl hydrocarbon is chloroform, methylene chloride or ethylene chloride.

5. A method according to claim 1, wherein in step(a) the mixing takes place for at least 15 seconds.

6. A method according to claim 1, wherein in step(c) the mixing is by centrifugedat about 6000 rpm for at least 5 minutes.

7. A method according to claim 1, wherein in step(d) the seperately recovering comprises removing the upper phase from the lower phase.

8. A method according to claim 1, wherein in step(d) the predetermined amount of the upper phase is about the same as the volume of the sample.

9. A method according to claim 1, wherein in step(e) the protien-precipitating agent is phosphotungstic acid, trichloroacetic acid, ammonium sulfate or a mixture therefore.

10. A method according to claim 1, wherein in step(e) the concentration of the protien precipitating agent is between 0.3 and 0.6 millgrams per milliliter.

11. A method according to claim 1, wherein in step(f) the mixing takes place for at least 5 seconds.

12. A method according to claim 1, wherein in step(h) the precipitate is washed with 500 ul of a saline solution to remove any trace of contaminants.

13. A method according to claim 1 wherein in step (k) the hydrolysis agent is resorcinol.

14. A method according to claim 1 wherein the step (l) the admixture is heated to a temperature of 115 to 120 degrees centigrade for 15 minutes.

15. A method according to claim 1 wherein step (m) the amount of lipid associated sialoprotein is determined by adding to the suspended precipitate a volume of resorcinol reagent, mixing, boiling for 15 minutes, adding a mixture of butylacetate and n-butanol (85:15 v/v) in a volume about twice said volume of resorcinol reagent mixing, centrifuging for about 5 minutes at above 2500 rpm, separating the organic layer, reading at 580 nm the extracted blue color present in the organic layer, determining the amount of lipid associated sialoprotein by comparing the reading obtained at 580 nm to that obtained for a standard having a known amount of lipid associated sialoprotein and applying the formula:

$$\frac{A \times B}{C}$$ Where $A$ = the concentration of lipid associated sialoprotein in the standard, B=the optical density of the sample and C=the optical density of the standard.

16. A method according to claim 15, wherein the volume of resorcinol reagent is about 0.5 ml.

17. A method of diagnosing cancer in a human subject which comprises determining the amount of lipid associated sialoprotein in a sample of the subject's cerebrospinal fluid, according to the method of claim 1 and comparing the amount so determined with amounts previously obtained for subjects known to have cancer by use of the method of claim 1.

18. A method of diagnosing cancer in a human subject which comprises determining at regular time intervals the amount of lipid associated sialoprotein in a sample of the subject's cerebrospinal fluid according to the method of claim 1 and comparing the amounts so determined with amounts previously obtained for the subject by use of the method of claim 1.

* * * * *